(12) United States Patent
Stock et al.

(10) Patent No.: US 10,314,817 B2
(45) Date of Patent: Jun. 11, 2019

(54) TRYPTAMIDE COMPOSITIONS AND METHODS OF USE

(71) Applicant: Signum Biosciences, Inc., Princeton, NJ (US)

(72) Inventors: Jeffry Stock, Monmouth Junction, NJ (US); Maxwell Stock, Monmouth Junction, NJ (US); Michael Voronkov, Monmouth Junction, NJ (US); Jose Fernandez, Monmouth Junction, NJ (US); Kristen Huber, Monmouth Junction, NJ (US)

(73) Assignee: Signum Biosciences, Inc., Monmouth Junction, NJ (US)

( * ) Notice: Subject to any disclaimer, the term of this patent is extended or adjusted under 35 U.S.C. 154(b) by 0 days.

(21) Appl. No.: 15/518,755

(22) PCT Filed: Oct. 15, 2015

(86) PCT No.: PCT/US2015/055745
§ 371 (c)(1),
(2) Date: Apr. 12, 2017

(87) PCT Pub. No.: WO2016/061357
PCT Pub. Date: Apr. 21, 2016

(65) Prior Publication Data
US 2017/0231955 A1  Aug. 17, 2017

Related U.S. Application Data

(60) Provisional application No. 62/121,711, filed on Feb. 27, 2015, provisional application No. 62/063,983, filed on Oct. 15, 2014.

(51) Int. Cl.
*A61K 31/405* (2006.01)
*C07D 209/16* (2006.01)

(52) U.S. Cl.
CPC .......... *A61K 31/405* (2013.01); *C07D 209/16* (2013.01)

(58) Field of Classification Search
CPC . A61K 31/405; A61K 2300/00; C07D 209/16
See application file for complete search history.

(56) References Cited

U.S. PATENT DOCUMENTS

2013/0156928 A1  6/2013  Bytof et al.

FOREIGN PATENT DOCUMENTS

DE    202008005965 U1    12/2008
EP       0714968 A2 *    6/1996

OTHER PUBLICATIONS

Folstar (J Agric. Food Chem 27, 1, 1979) (Year: 1979).*
Speer (Braz. J. Plant Pysiol. 18(1), 201-216, 2006). (Year: 2006).*
Basurto-Islas et al., Therapeutic benefits of a component of coffee in a rat model of Alzheimer's disease. Neurobiol Aging. Dec. 2014;35(12):2701-2712.
Caffeine Informer Staff, 20+ Harmful Effects of Caffeine. Retrieved online at: https://www.caffeineinformer.com/harmful-effects-of-caffeine. 5 pages, Nov. 9, 2017.
Center for Science in the Public Interest, Caffeine Chart. Retrieved online at: https://cspinet.org/eating-healthy/ingredients-of-concern/caffeine-chart. 11 pages, retrieved Oct. 9, 2018.
Lee et al., Neuroprotective and anti-inflammatory properties of a coffee component in the MPTP model of Parkinson's disease. Neurotherapeutics. Jan. 2013;10(1):143-53.
Supplementary European Search Report for Application No. 15850240.1, dated Apr. 6, 2018. 5 pages.
International Search Report for Application No. PCT/US2015/055745, dated Jan. 11, 2016. 3 pages.
International Preliminary Report on Patentability for Application No. PCT/US2015/055745, dated Apr. 27, 2017. 9 pages.

* cited by examiner

*Primary Examiner* — Umamaheswari Ramachandran
(74) *Attorney, Agent, or Firm* — McCarter & English, LLP; Peter Tu, Esq.; Maneesh Gulati, Esq.

(57) ABSTRACT

EHT extract including a mixture of late eluting tryptamides and early eluting tryptamides in a weight ratio of at least about 7:1 late eluting tryptamides:early eluting tryptamides, wherein the EHT extract includes at least 30% eicosanoyl-5-hydroxytryptamide, based on the total weight of the tryptamides in the EHT extract.

14 Claims, 4 Drawing Sheets

TRYPTAMIDE COMPOSITIONS AND METHODS OF USE

CROSS REFERENCE TO RELATED APPLICATIONS

This application is a 35 U.S.C. § 371 national stage filing of International Application No. PCT/US2015/055745, filed Oct. 15, 2015, which claims the benefit of U.S. Provisional Application No. 62/063,983, filed Oct. 15, 2014 and U.S. Provisional Application No. 62/121,711, filed Feb. 27, 2015. The contents of each of the foregoing applications are herein incorporated by reference in their entirety.

FIELD OF THE INVENTION

The present invention is directed to, among other things, extracts including a mixture of early eluting and late eluting tryptamides.

BACKGROUND

Tryptamides modulate protein phosphatase 2A (PP2A) to enhance brain health and its various cognitive functions. Currently tryptamides, more specifically eicosanoyl, docosanoyl and tetracosanoyl 5-hydroxytryptamides, are available for incorporation, in an un-isolated form, in the human diet, as trace amounts may be found in coffee and cocoa products.

More specifically, *Robusta* coffee beans may contain 565-1120 mg/kg and *Arabica* coffee beans may contain 500-2370 mg/kg of total tryptamides (Maier, 1981). However, human consumption of coffee can come in form of an aqueous extract providing only 0.6-0.8 mg of total trpytamindes per serving. The total tryptamides can include 13.26% of early eluting tryptamides and 86.74% of late eluting tryptamides with at least 40%, 41% and 3% of eicosanoyl, docosanoyl and tetracosanoyl tryptamides correspondingly.

Eicosanoyl 5-hydroxytryptamide levels in common coffee drinks are shown below in Table 1. Consumption of a serving of a commercial coffee drink can deliver between 0.6 to 0.72 mg of eicosanoyl 5-hydroxytryptamide.

TABLE 1

| Coffee Drink | eicosanoyl 5-hydroxytryptamide (mg/mL) | eicosanoyl 5-hydroxytryptamide per serving (mg) | Serving size (mL) |
|---|---|---|---|
| Espresso | 0.024 | 0.72 | 30 |
| Regular Coffee | 0.004 | 0.8 | 200 |
| Instant Coffee | 0.003 | 0.6 | 200 |

Furthermore, certain diterpenes, such as cafestol and kahweol, found in coffee are associated with promoting elevated cholesterol levels to the subject when administered, showing of at least an 8% increase in men and a 10% increase in women. In fact, coffee contains up to 0.6-1% of diterpenes that translates to 3-7 mg of diterpenes per serving in brewed coffee. Literature papers suggest that each 10 mg of diterpenes consumed per day can elevate serum cholesterol by 5 mg/dL. Therefore, 3-5 servings of coffee a day, which appear to be the minimum needed for the long term neuroprotection, may have some cardiovascular liabilities, particularly in subjects with underlying conditions—such as existing cardiovascular disease, smoking, a sedentary lifestyle and heredity factors—that make them prone to high cholesterol and/or other cardiovascular maladies.

Furthermore, coffee contains significant amounts of caffeine in amounts of 50-436 mg per serving and decaffeinated coffee about 2-25 mg per serving (http://www.cspinet.org/new/cafchart.htm). Caffeine is known to raise blood pressure in those already suffering from hypertension, cause insomnia, gout attack, indigestion, headaches, urinary incontinence, and reduce fertility in women. Caffeine overdose may lead to adverse symptoms, including death, especially in those with underlying medical conditions (http://www.caffeineinformer.com/harmful-effects-of-caffeine).

Similarly, cocoa liquor products contain 40.1 mg/kg of total tryptamides or about 1.6 mg per serving. Unfortunately, the bulk of tryptamides consists of docosanoyl and tetracosanoyl derivatives while cocoa products contain no biologically significant amounts of eicosanoyl 5-hydroxytryptamide, which has proven efficacy in various models of neurodegeneration, Parkinson and Alzheimer diseases.

There remains a need for a composition that includes all the benefits of tryptamides, but without the negative consequences such as elevated cholesterol levels and blood pressure.

There also remains a need for additional therapeutic agents that can protect against excitotoxic cell death. Over 1.7 million individuals, in the United States alone, suffer from traumatic brain injury (TBI) annually (Faul 2010). At risk groups for TBI include but are not limited to soldiers, athletes, car crash victims and domestic violence victims. (Hoge 2008; DeKosky 2010; McKee 2009; Valera 2003). It has been linked to diseases such as chronic traumatic encephalopathy, Alzheimer's disease, Parkinson's disease, amyotrophic lateral sclerosis, motor neuron disease and dementia (Mortimer 1991; Flemming 2000; Goldman 2006; Ben-Shlomo 1997; Chen 2007; Schmidt 2010). Post injury observations have shown glutamate levels increase by 2.8 fold (Faden 1989, Globus, 1995). A downstream effect of excessive glutamate exposure is the over activation of the AMPA (α-amino-3-hydroxy-5-methyl-4-isoxazolepropionic acid) receptor, NMDA (N-methyl-D-aspartate) receptor, and glutamate receptor leading to in an influx of Ca2+, oxidative stress and cellular damage ultimately resulting in excitotoxic cell death. This type of secondary injury has become a target for disease intervention. For example, memantine a non-toxic, non-phychotomimetic, NMDA receptor antagonist, is neuroprotective and has been used as a treatment for Alzheimer's and Parkinson's disease (Kornhuber 1994; Emre 2010; Merello 1999; Reisberg 2003). Nevertheless, additional therapies would be helpful.

The present invention seeks to address these unmet needs.

BRIEF SUMMARY OF THE INVENTION

One aspect of the present invention provides an EHT extract, wherein the EHT extract includes a mixture of late eluting tryptamides and early eluting tryptamides in a weight ratio of at least about 7:1 late eluting tryptamides:early eluting tryptamides, wherein the EHT extract includes at least 30% eicosanoyl-5-hydroxytryptamide, based on the total weight of the tryptamides in the EHT extract. In certain embodiments, the amount of caffeine in the EHT extract does not exceed about 15%, based on the total weight of the extract and/or the amount of diterpenes in the extract is less than about 1 mg/kg.

Compositions including an EHT extract, also referred to as EHT extract compositions, are also provided. The EHT extract compositions can further include one or more of a vitamin, a microelement, a food or health supplement, an herb extract, and a drug. In certain embodiments, the EHT extract composition includes a vitamin, a microelement, and a food or health supplement. In other embodiments, the EHT extract composition includes a vitamin, a microelement, a food or health supplement and an herb extract.

In one embodiment, the invention provides a formulation (e.g., a solid unit dosage such as a tablet) comprising 1.4-1.8 mg vitamin $B_6$ (pyridoxine HCl), 380-420 mcg folate (folic acid), 8-12 mcg of vitamin $B_{12}$ (cyanocobalamin), 14-18 mg magnesium, and 70-80 mg EHT extract. In another embodiment, the formulation comprises 1.6 mg vitamin $B_6$ (pyridoxine HCl), 400 mcg folate (folic acid), 10 mcg vitamin $B_{12}$ (cyanocobalamin), 16 mg magnesium, and 75 mg EHT extract. In alternative embodiments, the formulation consists essentially of, or consists of, vitamin $B_6$ (pyridoxine HCl), folate (folic acid), vitamin $B_{12}$ (cyanocobalamin), magnesium, and EHT extract.

In another embodiment, the invention provides a formulation (e.g., a solid unit dosage such as a tablet) comprising 1800-2200 IU vitamin D (cholecalciferol), 1.4-1.8 mg vitamin $B_6$ (pyridoxine HCl), 8-12 mcg vitamin $B_{12}$ (methylcobalamin), 14-18 mg magnesium, 68-72 mcg of selenium (selenomethionine), 48-52 mg alpha lipoic acid, 48-52 mcg huperzine A, and 30-40 mg EHT extract. In another embodiment, the formulation comprises 2000 IU vitamin D (cholecalciferol), 1.6 mg vitamin $B_6$ (pyridoxine HCl), 10 mcg vitamin $B_{12}$ (methylcobalamin), 16 mg magnesium, 70 mcg of selenium (selenomethionine), 50 mg alpha lipoic acid, 50 mcg huperzine A, and 35 mg EHT extract. In alternative embodiments, the formulation consists essentially of, or consists of, vitamin D (cholecalciferol), vitamin $B_6$ (pyridoxine HCl), vitamin $B_{12}$ (methylcobalamin), magnesium, selenium (as selenomethionine), alpha lipoic acid, huperzine A, and EHT extract.

In another embodiment, the invention provides a formulation (e.g., a solid unit dosage such as a tablet) comprising 1800-2200 IU vitamin D (cholecalciferol), 1.4-1.8 mg vitamin $B_6$ (pyridoxine HCl), 380-420 mcg of folate (folic acid), 8-12 mcg vitamin $B_{12}$ (cyanocobalamin), 14-18 mg magnesium, 68-72 mcg of selenium (selenomethionine), 48-52 mg alpha lipoic acid, 48-52 mcg huperzine A, and 30-40 mg EHT extract. In another embodiment, the formulation comprises 2000 IU vitamin D (cholecalciferol), 1.6 mg vitamin $B_6$ (pyridoxine HCl), 400 mcg of folate (folic acid), 10 mcg vitamin $B_{12}$ (cyanocobalamin), 16 mg magnesium, 70 mcg of selenium (selenomethionine), 50 mg alpha lipoic acid, 50 mcg huperzine A, and 35 mg EHT extract. In alternative embodiments, the formulation consists essentially of, or consists of, vitamin D (cholecalciferol), vitamin $B_6$ (pyridoxine HCl), folate (folic acid), vitamin $B_{12}$ (methylcobalamin), magnesium, selenium (selenomethionine), alpha lipoic acid, huperzine A, and EHT extract.

In another embodiment, the invention provides a formulation (e.g., a solid unit dosage such as a tablet) comprising 800-1000 IU vitamin D (cholecalciferol), 1.4-1.8 mg vitamin $B_6$ (pyridoxine HCl), 8-12 mcg vitamin $B_{12}$ (methylcobalamin), 14-18 mg magnesium, 68-72 mcg of selenium (selenomethionine), 98-102 mg of ginko biloba extract powder, 48-52 mg alpha lipoic acid, and 30-40 mg EHT extract. In another embodiment, the formulation comprises 1000 IU vitamin D (cholecalciferol), 1.6 mg vitamin $B_6$ (pyridoxine HCl), 10 mcg vitamin $B_{12}$ (methylcobalamin), 16 mg magnesium, 70 mcg of selenium (selenomethionine), 100 mg of ginko biloba extract powder, 50 mg alpha lipoic acid, and 35 mg EHT extract. In alternative embodiments, the formulation consists essentially of, or consists of, vitamin D (cholecalciferol), vitamin $B_6$ (as pyridoxine HCl), vitamin $B_{12}$ (methylcobalamin), magnesium, selenium (selenomethionine), ginko biloba extract powder, alpha lipoic acid and EHT extract.

In another embodiment, the invention provides a formulation (e.g., a solid unit dosage such as a tablet) comprising 800-1000 IU vitamin D (cholecalciferol), 1.4-1.8 mg vitamin $B_6$ (pyridoxine HCl), 8-12 mcg vitamin $B_{12}$ (methylcobalamin), 14-18 mg magnesium, 68-72 mcg of selenium (selenomethionine), 48-52 mg alpha lipoic acid, and 30-40 mg EHT extract. In another embodiment, the formulation comprises 1000 IU vitamin D (cholecalciferol), 1.6 mg vitamin $B_6$ (as pyridoxine HCl), 10 mcg vitamin $B_{12}$ (as methylcobalamin), 16 mg magnesium, 70 mcg of selenium (selenomethionine), 50 mg alpha lipoic acid, and 35 mg EHT extract. In alternative embodiments, the formulation consists essentially of, or consists of, vitamin D (cholecalciferol), vitamin $B_6$ (pyridoxine HCl), vitamin $B_{12}$ (methylcobalamin), magnesium, selenium (selenomethionine), alpha lipoic acid and EHT extract.

In another embodiment, the invention provides a formulation (e.g., a solid unit dosage such as a tablet) comprising 1800-2200 IU vitamin D (cholecalciferol), 34-39 mg vitamin C, 1.4-1.8 mg vitamin $B_6$ (pyridoxine HCl), 8-12 mcg vitamin $B_{12}$ (cyanocobalamin), 14-18 mg magnesium, 82-86 mcg of selenium (selenium yeast), 135-139 mg ginko biloba extract powder, and 30-40 mg EHT extract. In another embodiment, the formulation comprises 2000 IU vitamin D (cholecalciferol), 36.36 mg vitamin C, 1.6 mg vitamin $B_6$ (as pyridoxine HCl), 10 mcg vitamin $B_{12}$ (cyanocobalamin), 16 mg magnesium, 84 mcg of selenium (selenium yeast), 137.50 mg ginko biloba extract powder, and 35 mg EHT extract. In alternative embodiments, the formulation consists essentially of, or consists of, vitamin D (cholecalciferol), vitamin C, vitamin $B_6$ (pyridoxine HCl), vitamin $B_{12}$ (cyanocobalamin), magnesium, selenium (selenium yeast), ginko biloba extract powder and EHT extract.

Another aspect of the present invention provides a method of treating traumatic brain injury or an encephalopathy in a subject in need thereof that includes administering to the subject an effective amount of a composition described herein.

DETAILED DESCRIPTION

The use of headings and subheadings in this section (or any other section of this application) is solely for convenience of reference and not intended to be limiting.

Definitions

As used herein, tryptamides refer to the compounds that are encompassed within formula (I):

(I)

wherein n is 14-22, and one or more of the CH$_2$ groups in the (CH$_2$)$_n$ group can optionally be replaced with CH to provide one or more double bonds.

Early eluting tryptamides, as used herein, refer to tryptamides, as defined above, that elute on a reverse phase column prior to eicosanoyl 5-hydroxytryptamide. Tryptamides having less than 20 total carbons in the alkyl chain less (i.e., n in Formula (I) is less than 18) are early eluting tryptamides. Typically, early eluting tryptamides have <40° C. melting points and have a butter-like consistency.

Late eluting tryptamides, as used herein, refer to tryptamides, as defined above, that elute on a reverse phase column after eicosanoyl 5-hydroxytryptamide, and includes eicosanoyl 5-hydroxytryptamide itself. Tryptamides having 20 or more total carbons in the alkyl chain (i.e. n in Formula (I) is 18 or more) are late eluting tryptamides. Eicosanoyl, docosanoyl and tetracosanoyl 5-hydroxytryptamides, all of which are examples of late eluting tryptamides, elute on a reverse phase column after the early eluting tryptamides. Typically late eluting tryptamides have >40° C. melting points and are solids.

For example, eicosanoyl 5-hydroxytryptamide, which is shown below, is a late eluting tryptamide and the total number of carbons in the alkyl chain is 20:

As used herein, "diterpenes" refers to compounds that encompassed within formula (II):

(II)

wherein the dashed line can be present or absent.

As used herein the term "EHT extract" refers to a coffee extract comprising a mixture of early eluting and late eluting tryptamides. In certain embodiments, an EHT extract refers to a mixture of early eluting and late eluting coffee tryptamides in the ratio of at least about 1:7, 1:8, 1:9, 1:10, 1:25, 1:50, 1:75 and up to 1:100 with at least 30%, or 35%, 40%, 45% or 50% of eicosanoyl-5-hydroxytryptamide, based on the weight of all the tryptamides in the composition. Additionally, for purposes brevity, an EHT extract, as used herein, can also be read to refer to alternative embodiments in which EHT extract refers to any component that includes eicosanoyl-5-hydroxytryptamide (such as an extract derived from coffee bean or coffee that contains eicosanoyl-5-hydroxytryptamide) or eicosanoyl-5-hydroxytryptamide itself, whether isolated from an organic starting material or prepared synthetically).

Traumatic brain injury (TBI), also known as intracranial injury, occurs when an external force traumatically injures the brain. TBI can be classified based on severity, mechanism (closed or penetrating head injury), or other features (e.g., occurring in a specific location or over a widespread area). Head injury usually refers to TBI, but is a broader N-(2-(5-hydroxy-1H-indol-3-yl)ethyl)stearamide or "18-5HT", shown below, is an early eluting tryptamide and the total number of carbons in the alkyl chain is 18:

category because it can involve damage to structures other than the brain, such as the scalp and skull. TBI could be related to head injuries sustained in combat, equestrian, military training, falls, sports (contact and solo), shock wave exposures (single or multiple small), bicycle and motor vehicle accidents.

Chronic traumatic encephalopathy (CTE) is a form of encephalopathy that is a progressive degenerative disease, which can currently only be definitively diagnosed postmortem, in individuals with a history of multiple concussions and other forms of head injury.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the invention, "an effective amount" of at least one compound is administered to a subject (e.g., a mammal). As understood by the person of ordinary skill in this art, "effective amount" will vary, depending on the compound or composition, the disease (and its severity), the treatment desired, age and weight of the subject, etc.

The EHT extract, can in certain embodiments, have a reduced amount of caffeine not to exceed about 15%, or 10%, or 5%, based on the total weight of the extract. In certain embodiments, the amount of caffeine in the EHT extract is not to exceed 2 mg, 3 mg, 4 mg, 5 mg, 6 mg, 7 mg, 8 mg, 9 mg, or 10 mg per serving or unit dosage.

In yet another embodiment, the EHT extract, such as any one of the EHT extracts described above, has a reduced amount of diterpenes. For example, in one embodiment, the EHT extract has of no more than about 2 mg of diterpenes per kg of EHT extract. In one embodiment, the EHT extract has no more than about 1 mg of cafestol per kg of EHT Extract, or less than about 0.12 mg of cafestol per serving or unit dosage of EHT extract.

In a further embodiment, EHT extract is administered, as part of a composition, in a solid dosage form. For example, the solid dosage form can be a tablet, a capsule, a sachet, a powder, or in the form of a solid food. In certain embodiments, the amount of EHT extract administered, such as in a solid dosage form, can be between 1 mg and 2 grams per daily serving or unit dosage (e.g., 1 mg, 5 mg, 10 mg, 25 mg, 50 mg, 75 mg, 100 mg, 250 mg, 500 mg, 1 g, 1.5 g, or 2 g).

In a still further embodiment, EHT extract is administered in a liquid dosage form as a drink, syrup, suspension, emulsion, tincture, elixir, tea, effervescent formulation and so on. For example, the EHT extract can be administered in a liquid dosage form, and the amount of EHT extract in the composition can be, in certain embodiments, so as to provide no less than 1 mg and no more than about 2 grams per daily serving or unit dosage.

Whether administered as a solid or a liquid dosage form, the EHT extract can be administered together with vitamins (e.g., vitamin A, vitamin $B_1$, vitamin $B_2$, vitamin $B_3$, vitamin $B_5$, vitamin $B_6$, vitamin $B_7$, vitamin $B_9$ (folic acid or folate), vitamin $B_{12}$, vitamin C, vitamin D, vitamin E, vitamin K), microelements (e.g., iodine, iron, magnesium, chromium, calcium, selenium, zinc, manganese, potassium), food and health supplements (e.g., N-acetyl L-cysteine, acetyl L-carnitine, S-adesnosyl methionine, vinpocetine, huperzine A, L-theanine, phosphatidylserine, bacopa, pterostilbene, L-tyrosine, L-glutamine, bacopin, L-pyroglutamic acid, phosphatidylserine, docosahexaenoic acid, choline, inositol, N-acetyltyrosine, gamma-aminobutyric acid, activin, L-alpha glycerylphosphorylcholine, citicoline,) herb parts (e.g., leafs, roots, buds, flowers, stem or the like) or herb, fruit or botanical extracts (e.g., green tea extract, bilberry fruit standardized extract, grape skin extract, guarana extract, kola nut extract, peppermint oil, tulsi extract (holy basil), green tea extract, gingko *biloba* extract, *rhodiola* extract, white tea extract, black tea extract, *panax ginseng*), pharmaceutically acceptable excipients (e.g., microcrystalline cellulose, dicalcium pho spate, stearic acid, magnesium stearate, croscarmellose sodium, silicon dioxide, enteric coating, natural flavors, gelatin, titanium dioxide, white rice flour, salt, acetic acid, disodium EDTA, rice bran oil, vegetable wax, gelatin, glycerin, water, colors (e.g., annatto, carmine, carob), cellulose, water, dicalcium phosphate, pharmaceutical glaze, starch, maltodextrin, vegetable cellulose, sunflower lecithin, safflower oil, glycerin, sunflower lecithin, sorbitol, modified food starch), and drugs (e.g., piracetam, ADHD medications, xanthines, nicotine, tianeptine, cholinergic agents valproates, pramiracetam, oxiracetam, coluracetam, and aniracetam).

In certain embodiments, the EHT extract is included in a composition (i.e., an EHT extract composition) that further includes at least one vitamin selected from vitamin D, vitamin $B_6$, vitamin $B_9$, vitamin $B_{12}$ and vitamin C. Alternatively, the EHT extract composition can include at least two, or at least three vitamins selected from vitamin D, vitamin $B_6$, vitamin $B_9$, vitamin $B_{12}$ and vitamin C. In one embodiment, the EHT extract composition includes vitamin D, vitamin $B_6$, and vitamin $B_{12}$. In a further embodiment, the EHT extract composition includes vitamin D, vitamin $B_6$, vitamin $B_{12}$ and vitamin C. In a still further embodiment, the EHT extract composition includes vitamin D, vitamin $B_6$, vitamin $B_9$ and vitamin $B_{12}$.

In one embodiment, the vitamin D is included as cholecalciferol (vitamin $D_3$). Similarly, vitamin $B_6$ can be included as pyridoxine HCl, and vitamin $B_{12}$ can be included as methylcobalamin. Alternatively, other forms of these vitamins can also be included in addition to the above-described forms, or in their place.

In EHT extract compositions including vitamin $B_6$, the vitamin $B_6$ can be provided in the composition in an amount so as to provide, in a unit dosage or serving, from about 250 micrograms to about 5 mg, or from about 750 micrograms to about 3 mg, or from about 1 mg to about 2 mg (e.g., about 1.6 mg) of vitamin $B_6$. Alternatively, other amounts of vitamin $B_6$ can be included.

In EHT extract compositions including vitamin $B_9$, the vitamin $B_9$ can be provided in the composition in an amount so as to provide, in a unit dosage or serving, from about 50 micrograms to about 1 mg, or from about 100 micrograms to about 750 micrograms, or from about 200 micrograms to about 600 micrograms (e.g., about 400 micrograms) of vitamin $B_9$. Alternatively, other amounts of vitamin $B_9$ can be included.

In EHT extract compositions including vitamin $B_{12}$, the vitamin $B_{iz}$ can be provided in the composition in an amount so as to provide, in a unit dosage or serving, from about 1 microgram to about 100 microgram, or from about 2.5 micrograms to about 25 micrograms, or from about 5 micrograms to about 15 micrograms (e.g., about 10 micrograms) of vitamin $B_{12}$. Alternatively, other amounts of vitamin $B_{12}$ can be included.

In EHT extract compositions including vitamin D, the vitamin D can be provided in the composition in an amount so as to provide, in a unit dosage or serving, from about 250 IU to about 6000 IU, or from about 500 IU to about 5000 IU, or from about 750 IU to about 2500 IU (e.g., about 1000 IU, about 2000 IU) of Vitamin D. Alternatively, other amounts of vitamin D can be included.

In certain embodiments, the EHT extract composition includes at least one microelement selected from magnesium and selenium. For example, the EHT extract composition can include both magnesium and selenium. The magnesium can be included as magnesium citrate, or other pharmaceutically acceptable salts of magnesium can be included. Similarly, selenium can be included as selenomethionine, although the inorganic form of selenium (selenite) can also be included. Selenium can also be included as selenium yeast.

In EHT extract compositions including magnesium, the magnesium can be provided in the composition in an amount so as to provide, in a unit dosage or serving, from about 500 micrograms to about 100 mg, or from about 1 mg to about 30 mg, or from about 8 mg to about 24 mg (e.g., about 16 mg) of magnesium. Alternatively, other amounts of magnesium can be included. As would be understood by one of ordinary skill in the art, when magnesium is included as a pharmaceutically acceptable salt of magnesium (e.g., magnesium citrate) dosage amounts need to be adjusted according to stoichiometry (e.g., 100 mg of magnesium citrate yields 16 mg of magnesium).

In EHT extract compositions including selenium, the selenium can be provided in the composition in an amount so as to provide, in a unit dosage or serving, from about 1 microgram to about 500 mg, or from about 10 micrograms to about 400 micrograms, or from about 40 micrograms to about 100 micrograms (e.g., about 70 micrograms or about 84 micrograms) of selenium. Alternatively, other amounts of selenium can be included.

In certain embodiments, the EHT extract composition includes ginko biloba, such as a ginko biloba extract powder. For example, from about 1 mg to about 750 mg, or from about 10 mg to about 400 mg, or from about 100 mg to about 170 mg (e.g., about 137.50 mg) of ginko biloba can be included. Alternatively, other amounts of ginko biloba can be included.

In certain embodiments, the EHT extract composition includes at least one health supplement selected from alpha lipoic acid, and Huperzine A. For example, the EHT extract composition can include both alpha lipoic acid and Huperizine A.

In EHT extract compositions including alpha lipoic acid, the alpha lipoic acid can be provided in the composition in an amount so as to provide, in a unit dosage or serving, from about 1 mg to about 1.3 g, or from about 2.5 mg to about 500 mg, or from about 25 mg to about 75 mg (e.g., about 50 mg) of alpha lipoic acid. Alternatively, other amounts of alpha lipoic acid can be included.

In EHT extract compositions including Huperzine A, the Huperzine A can be provided in the composition in an amount so as to provide, in a unit dosage or serving, from about 1 mg to about 1 g, or from about 2.5 mg to about 500 mg, or from about 25 mg to about 75 mg (e.g., about 50 mg) of Huperzine A. Alternatively, other amounts of Huperzine A can be included.

In certain embodiments, the EHT extract can be present in the amounts of 1 mg to 1 gram per kg of composition. The EHT extract provided in the composition, in certain embodiments, is in an amount so as to provide, in a unit dosage or serving, from about 1 mg to about 150 mg, or from about 5 mg to about 75 mg, or from about 10 mg to about 60 mg (e.g., 35 mg) of EHT extract.

As noted, the EHT extract can be administered together with, for example, B vitamins (e.g., vitamin $B_6$, vitamin $B_9$ (folic acid), vitamin $B_{12}$). In some embodiments, the B vitamins can collectively be present in the amounts from about 1 micrograms to 10 mg, or from about 50 micrograms to about 5 mg per unit dosage or serving. The EHT extract can further include one or more of magnesium and selenium, or both magnesium and selenium, and, optionally, can still further include one or more herb, fruit or botanical extracts (e.g. ginko biloba, and extracts of huperizia serrate, such as huperzine A).

In one embodiment, a composition comprising an effective amount of an EHT extract is administered to a subject suffering from a traumatic brain injury (TBI) to treat the traumatic brain injury. In one embodiment, an effective amount of eicosanoyl 5-hydroxytryptamide is administered to a subject suffering from a traumatic brain injury (TBI) to treat the traumatic brain injury. The EHT extract or eicosanoyl 5-hydroxytryptamide can be administered, for example, orally or parenterally (e.g., IV).

In another embodiment, a composition comprising an effective amount of an EHT extract is administered to a subject suffering from, or at risk of developing, an encephalopathy to treat the encephalopathy. In one embodiment, an effective amount of eicosanoyl 5-hydroxytryptamide is administered to a subject suffering from an encephalopathy to treat the encephalopathy. The encephalopathy can be, for example, chronic traumatic encephalopathy (CTE). The EHT extract or eicosanoyl 5-hydroxytryptamide can be administered, for example, orally or parenterally (e.g., IV).

In another embodiment, EHT extract is administered to a subject at a risk of developing a TBI, or at risk of developing an encephalopathy (e.g., CTE) due to inflammation, infection, vascular irregularities, autoimmune disorders, metabolic disorders, and hereditary factors.

In yet another embodiment, EHT extract is administered to a subject at a risk of cardiovascular disease, metabolic syndrome, pulmonary disorders, endocrine disorders, autoimmune disorders, inflammation, infection, hepatic disorders, renal disorders, neoplastic disorders, musculoskeletal disorders, gastrointestinal disorders, genitourinary disorders, sexual disorders, functional disorders, genetic liabilities, nutritional insufficiences, environmental and toxin exposures, and drug reaction/exposure.

An effective amount of EHT extract can be determined by one of ordinary skill in the art, based in part on the amount of eicosanoyl 5-hydroxytryptamide contained in the EHT extract. It is noted, however, that because the EHT extract can contain other active components, such as docosanoyl and tetracosanoyl 5-hydroxytryptamides, a lower amount of eicosanoyl 5-hydroxytryptamide may be required, as compared to when administering eicosanoyl 5-hydroxytryptamide alone.

For example, an effective amount of EHT extract can be an amount of EHT that provides 0.1 mg/day or more of eicosanoyl 5-hydroxytryptamide. In certain embodiments, the EHT extract is administered so as to provide, for example, 0.1 mg/day, 5 mg/day, 10 mg/day, 20 mg/day, 25 mg/day, 50 mg/day, or 100 mg/day of eicosanoyl 5-hydroxytryptamide. For example, 3 mg/kg body weight—120 mg/kg body weight of EHT extract can be administered orally or parenterally (e.g., IV) to a subject according to instantly described methods of treatment.

EXAMPLE 1

Preparation of an EHT Extract

Commercially available coffee wax (7 kg) was charged to a 20 L jacketed glass reactor equipped with a mechanical stirrer and thermocouple. Hot water (10 L, 75° C.) was added and the temperature was maintained at 70-75° C. for 2 hours. Once formation of two layers was observed, the water layer was drained through the bottom valve. The hot water wash was repeated once more, and at this point isopropanol (16 L, 99.9%) was charged to the reactor. The mixture is then heated to 75° C. while being vigorously stirred for 2 hours. The stirrer was stopped and the mixture was cooled to 4° C. overnight then crude product is then collected on a glass filter, dried and then transferred to the vacuum oven for 36 hours (or until constant weight) to yield crude coffee extract (1.2 kg; 10% tryptamides).

The crude coffee extract (5 kg, from above) was added through a loading valve to a 20 L jacketed glass reactor equipped with a stirrer followed isopropanol (10 L, 99%) and heated to 75° C. The temperature was maintained for additional 1 hr while stirring to make sure that the coffee extract was completely dissolved. Then the isopropanol solution was dispensed via bottom valve in to a crystallization vessel and cooled to room temperature overnight. The product is collected by filtration on glass filter (5 L, Chemglass) in three batches and dried in a vacuum oven to a constant weight (about 36 hrs). The final product (3.4 kg, 68% yield) was packed (milling is optional) in double polyethylene bags in a plastic container.

EXAMPLE 2

HPLC Analysis of an EHT Extract

Figure 1:
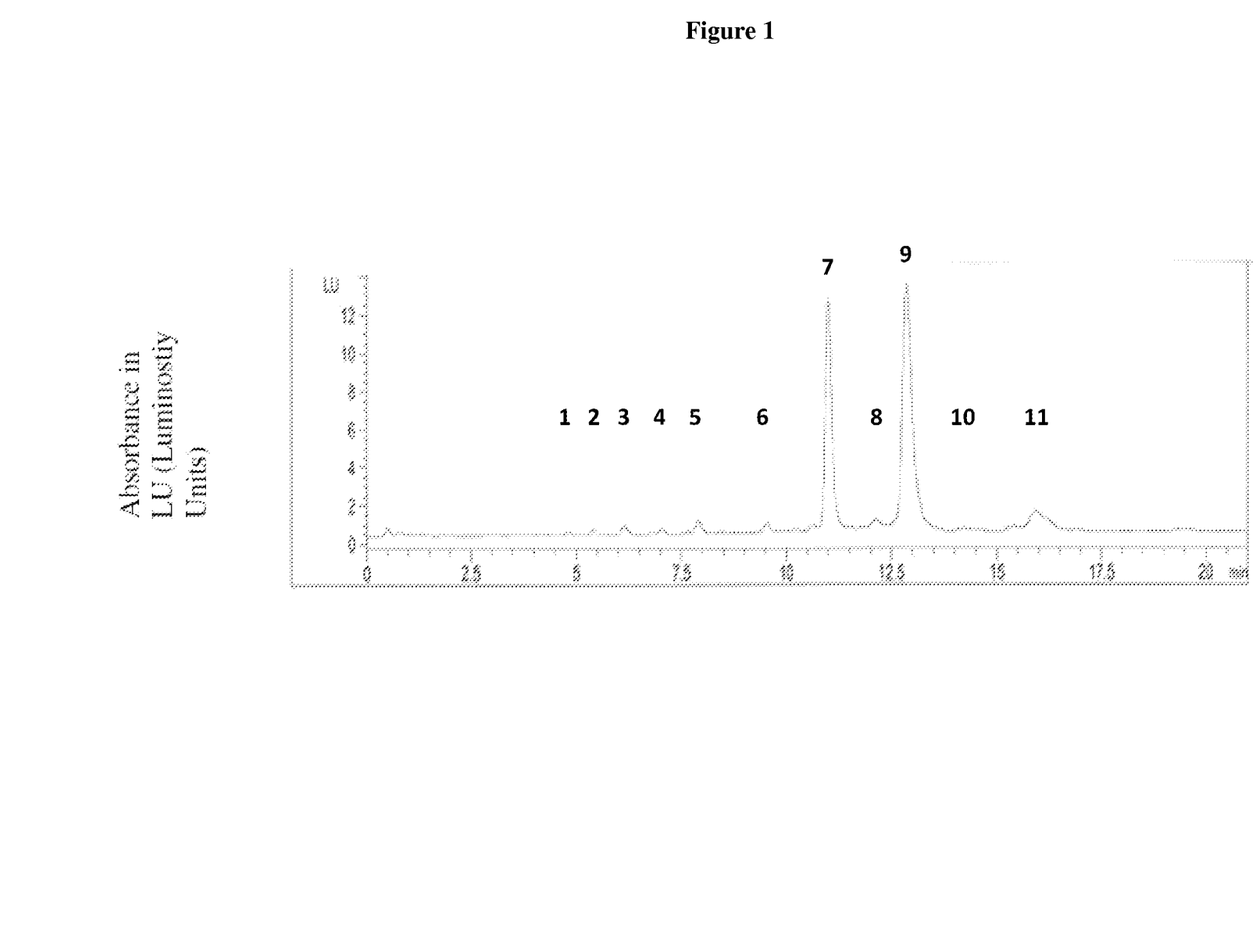
FIG. 1 depicts an HPLC analysis of a composition of the present invention. The levels of corresponding tryptamides are quantified and listed in Table 2.

FIG. 1 depicts an HPLC analysis of an EHT extract according to the present invention, prepared as described in Example 1. The HPLC analysis was performed as generally described in Braz. J. Plant Physiol., 18(1):201-216 (2006) by Karl Speer et al. and hereby incorporated by reference, in which fluorescence detection at an excitation wavelength of 280 nm and an emission wavelength of 330 nm was employed. The levels of corresponding tryptamides are quantified and listed in Table 2. Tryptamides 1-6 are early eluting tryptamides and 7-11 (12 and 13 are not found in EHT extract in quantifiable amounts) are late eluting tryptamides.

Levels of tryptamides in coffee, cocoa and an EHT extract according to the present invention, prepared as described in Example 1. Tryptamides 4, 12 and 13 were not detected in EHT extract in quantifiable amounts.

EXAMPLE 3

Determination of Cafestol and Kahweol Levels in an EHT Extract

HPLC Method.

High performance liquid chromatography analysis was performed on an Agilent 1200 instrument using a Phenomenex Luna C18 3u 50 mm×4.6 mm with C18 Guard column at room temperature. The mobile phase was Solvent A: HPLC grade water with 0.05% TFA (hereinafter "Solvent A") and Solvent B: HPLC grade acetonitrile with 0.05% TFA with a 1 mL per minute flow rate (hereinafter "Solvent B"). The gradient was set as follows: start with 0% Solvent B, then 99% Solvent B at 16 min, followed 99% Solvent B for 10 min. Peaks were quantified by fluorescence using 214 nm for cafestol and 254 nm for kahweol, the peak area was compared to the previously determined corresponding standard curves. The retention time for cafestol was 11.77 min and for kahweol was 11.67 min.

A standard curve was run using synthetic cafestol (Aldrich) and kahweol (Aldrich). Lower limit of detection for cafestol was determined to be at 0.5 µg/mL. The lower limit of quantification for cafestol was determined to be 1 µg/mL. Lower limit of detection (LLOD) for kahweol was determined to be at 1 µg/mL. The lower limit of quantification for kahweol (LLOQ) was determined to be 2 µg/mL.

Sample Preparation and Calculations:

A sample of EHT extract (1.1 mg, prepared as described in Example 1) was dissolved in DMSO (1 mL), warmed up to 40° C. and vortexed for 5 min. 10 µL of this solution was injected in HPLC. No peak at 11.67 min and a small peak (6.2 iu) at 11.77 min was observed in three consecutive runs. To verify the 11.77 min peak as cafestol, its analytical standard was spiked into a EHT sample and run again. Again, a single peak was observed at 11.77 min and it was identified as cafestol. Using an equation derived from a cafestol standard curve it was determined that 1 mg of EHT extract contains about 1.58 µg of cafestol. The amount of kahweol in the EHT extract was below the LLOD.

TABLE 2

| | | Coffee (published) | | | Cocoa (published) | | | EHT Extract | | |
|---|---|---|---|---|---|---|---|---|---|---|
| | | Area | % | % | Area | % | % | Area | % | % |
| Early tryptamides | 1 18:2-5HT | 1 | 0.23 | 13.26 | — | — | 0.00 | 1 | 0.25 | 3.97 |
| | 2 16-5HT | 1 | 0.23 | | | | | 2.99 | 0.76 | |
| | 3 20(OH)-5HT | 17 | 3.95 | | | | | 5.24 | 1.34 | |
| | 4 20:1-5HT | 14 | 3.26 | | | | | | | |
| | 5 18-5HT | 17 | 3.95 | | | | | 6.36 | 1.62 | |
| | 6 22(OH)-5HT | 7 | 1.63 | | | | | 5.19 | 1.32 | |
| Late tryptamides | 7 20-5HT | 173 | 40.23 | 86.74 | — | — | 96.99 | 125.72 | 32.03 | 94.71 |
| | 8 21-5HT | 3 | 0.70 | | 0.3 | 0.15 | | 5.6 | 1.43 | |
| | 9 22-5HT | 179 | 41.63 | | 61 | 30.61 | | 212.41 | 54.12 | |
| | 10 23-5HT | 2 | 0.47 | | 5 | 2.51 | | 1.88 | 0.48 | |
| | 11 24-5HT | 16 | 3.72 | | 125 | 62.72 | | 26.1 | 6.65 | |
| | 12 25-5HT | — | — | | 2 | 1.00 | | — | — | |
| | 13 25-5HT | — | — | | 6 | 3.01 | | — | — | |

EXAMPLE 4

EHT Extract Tablets

EHT extract from Example 1 are combined with pyridoxine HCl, folic acid, cyanocobalamin, and magnesium citrate and placed into a blender and blended until uniformly mixed. Granulation was not observed. The blended formulation is then placed into a standard tablet press and compressed into tablets. The amounts of Vitamin $B_6$, folic acid, cyanocobalamin and magnesium citrate in the bulk formulation are selected so as to yield, as a unit dosage to be orally administered by a subject, a tablet as described below in Table 3.

TABLE 3

Supplement Facts
Serving Size: 1 Tablet (e.g., one tablet/day)

| | Amount per Serving | % Daily Value |
|---|---|---|
| Vitamin $B_6$ (as pyridoxine HCl) | 1.6 mg | 80% |
| Folate (as folic acid) | 400 mcg | 100% |
| Vitamin $B_{12}$ (as cyanocobalamin) | 10 mcg | 4% |
| Magnesium (from 100 mg magnesium citrate) | 16 mg | 4% |
| EHT extract | 75 mg | * |

* Daily value not established.

The coating solutions described below are introduced with hot air to form a coating mix to be applied to the freshly pressed tablets in a tablet coating machine. The coated tablets are dried under controlled conditions to prepare the final unit dosage forms.

Vanilla coating only: dicalcium phosphate, microcrystalline cellulose, croscarmellose sodium, stearic acid, coating (hypromellose, talc, titanium dioxide, polyethylene glycol, saccharin sodium, natural flavor, sucralose), magnesium stearate and silica.

Red coating only: Dicalcium Phosphate, microcrystalline cellulose, croscarmellose sodium, stearic acid, coating (polyvinyl alcohol, polyethylene glycol, FD&CF #40, talc and titanium dioxide), magnesium stearate and silica.

Vanilla and red coating: Dicalcium phosphate, microcrystalline cellulose, croscarmellose sodium, stearic acid, coating (polyvinyl alcohol, macrogol, FD&C red #40 lake, talc, titanium dioxide, vanillin), magnesium stearate and silica.

By the same process, the tablet formulations listed below in Tables 4-8 are also prepared. In each of these tables, one serving is one tablet, which is instructed to be administered once daily.

TABLE 4

| | Amount per Serving | % Daily Value |
|---|---|---|
| Vitamin D (as cholecalciferol) | 2000 IU | 500% |
| Vitamin $B_6$ (as pyridoxine HCl) | 1.6 mg | 80% |
| Vitamin $B_{12}$ (as methylcobalamin) | 10 mcg | 167% |
| Magnesium (from 100 mg magnesium citrate) | 16 mg | 4% |
| Selenium (as selenomethionine) | 70 mcg | 100% |
| Alpha lipoic acid | 50 mg | * |
| Huperzine A ((from *huperzia serrata* whole plant extract)) | 50 mcg | * |
| EHT extract | 35 mg | * |

* Daily value not established.

TABLE 5

| | Amount per Serving | % Daily Value |
|---|---|---|
| Vitamin D (as cholecalciferol) | 2000 IU | 500% |
| Vitamin $B_6$ (as pyridoxine HCl) | 1.6 mg | 80% |
| Folate (as folic acid) | 400 mcg | 100% |
| Vitamin $B_{12}$ (as cyanocobalamin) | 10 mcg | 167% |
| Magnesium (from 100 mg magnesium citrate) | 16 mg | 4% |
| Selenium (as selenomethionine) | 70 mcg | 100% |
| Alpha lipoic acid | 50 mg | * |
| Huperzine A (from *huperzia serrata* whole plant extract) | 50 mcg | * |
| EHT extract | 35 mg | * |

* Daily value not established.

TABLE 6

| | Amount per Serving | % Daily Value |
|---|---|---|
| Vitamin D (as cholecalciferol) | 1,000 IU | 500% |
| Vitamin $B_6$ (as pyridoxine HCl) | 1.6 mg | 80% |
| Vitamin $B_{12}$ (as methylcobalamin) | 10 mcg | 167% |
| Magnesium (from 100 mg magnesium citrate) | 16 mg | 4% |
| Selenium (as selenomethionine) | 70 mcg | 100% |
| *Ginko Biloba* extract powder | 100 mg | * |
| Alpha lipoic acid | 50 mg | * |
| EHT extract | 35 mg | * |

* Daily value not established.

TABLE 7

| | Amount per Serving | % Daily Value |
|---|---|---|
| Vitamin D (as cholecalciferol) | 1,000 IU | 500% |
| Vitamin $B_6$ (as pyridoxine HCl) | 1.6 mg | 80% |
| Vitamin $B_{12}$ (as methylcobalamin) | 10 mcg | 167% |
| Magnesium (from 100 mg magnesium citrate) | 16 mg | 4% |
| Selenium (as selenomethionine) | 70 mcg | 100% |
| Alpha lipoic acid | 50 mg | * |
| EHT extract | 35 mg | * |

* Daily value not established.

TABLE 8

| | Amount per Serving | % Daily Value |
|---|---|---|
| Vitamin D (as cholecalciferol) | 2000 IU | 500% |
| Vitamin C | 36.36 mg | 4.85% |
| Vitamin $B_6$ (as pyridoxine HCl) | 1.6 mg | 80% |
| Vitamin $B_{12}$ (as cyanocobalamin) | 10 mcg | 167% |
| Magnesium (from 100 mg magnesium citrate) | 16 mg | 4% |
| Selenium (as selenium yeast) | 84 mcg | 100% |
| *Ginko Biloba* extract powder | 137.50 mg | * |
| EHT extract | 35 mg | * |

* Daily value not established.

EXAMPLE 5

EHT Extract Aqueous Formulation

Two grams of EHT extract, prepared as described in Example 1, were melted together with 3 grams of 2-hydroxyethyl 12-hydroxyoctadecanoate (Solutol HS15) and 2 grams of Polyoxyethylene (20) sorbitan monooleate (Tween-80) under vigorous stirring at 70° C. to produce very viscous dark brown syrup. The syrup was further mixed with small amount of hot water and stirred until uniform. Upon cooling this syrup was further diluted with water to the needed concentration. Unexpectedly the thus produced aqueous EHT extract can improve its oral bioavailability.

Table 9, below, provides a pharmacokinetic description of this aqueous EHT extract. As noted, it shows that the aqueous formulation, as described in this Example, unexpectedly gives an improvement in oral bioavailability, as compared to a non-aqueous EHT formulation prepared based on extraction with DMSO and not processed with 2-hydroxyethyl 12-hydroxyoctadecanoate and Polyoxyethylene (20) sorbitan monooleate.

TABLE 9

| Test Article | Route of Administration | Dose (mg/kg) | Subject | T½ (min) | Tmax (min) | Cmax (ng/mL) | AUCINF (min * ng/mL) | F (%) |
|---|---|---|---|---|---|---|---|---|
| EHT (DMSO) | IV | 1 | mice | 106 | — | — | 66371 | — |
| EHT (DMSO) | PO | 5 | mice | 75 | 60 | 67 | 5074 | 2 |
| Aqueous EHT | IV | 5 | rat | 451 | — | — | 30322 | — |
| Aqueous EHT | PO | 5 | rat | 762 | 30 | 104 | 4664 | 15% |
| Esspresso | PO | 0.12 | human | 188 | 248 | 2 | 3751 | — |

EXAMPLE 6

Use of EHT Extract to Treat TBI and CTE

Figure 2:
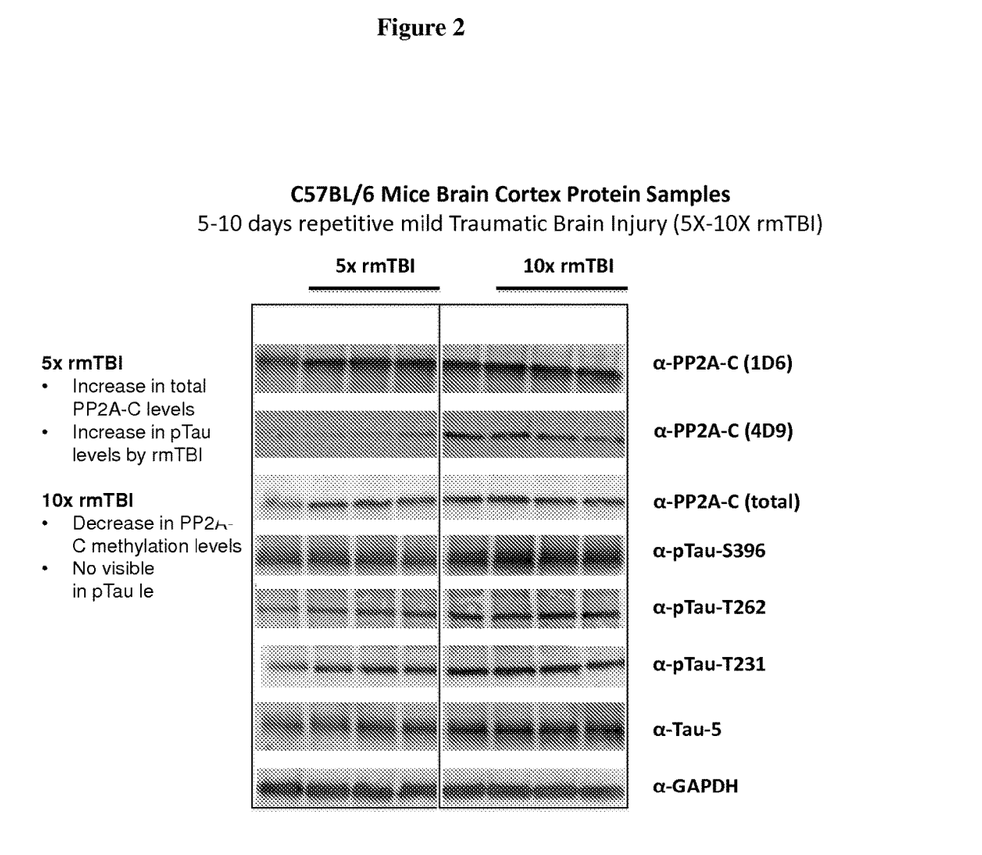
FIG. 2 depicts that short-term TBI causes increases in pTau levels and longer-term TBI causes PP2A demethylation.
Figure 3:
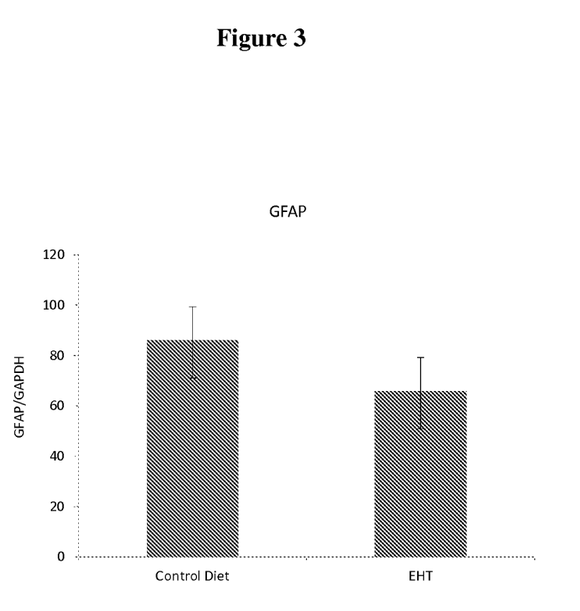
FIG. 3 demonstrates that GFAP serves as a biomarker for TBI and CTE and that EHT administered to animals as diet unexpectedly lowers GFAP in mouse brain after TBI.

FIG. 2. demonstrates that short term TBI causes increases in pTau levels and longer term TBI causes PP2A demethylation. Papa teaches that glial fibrillary acidic protein (GFAP) is released into serum following a traumatic brain injury (TBI), and can be used in detecting intracranial CT lesions, particularly in the setting of extracranial fractures J. Neurotrauma. 2014 Nov. 15; 31 (22): 1815-22. PMID 24903744).

Thus, GFAP serves as a biomarker for TBI and CTE. FIG. 2 shows that EHT extract, prepared as described in Example 1 and administered to mice with a TBI. The mice are estimated to receive about 5 grams of 0.1% EHT extract per day via their rodent chow for about 3 weeks. It is found that this group of mice receiving the EHT extract showed unexpectedly lower GFAP in mouse brain after TBI, as compared to a control diet group, in which the EHT extract was not administered.

EXAMPLE 7

Primary Neuronal Cell Culture

Primary neuronal cultures of cerebral cortex were obtained from rat embryos (E17) according to Brewer 1995. Cells in Neurobasal® Medium supplemented with 2% B27, glutamine, and pen-strep antibiotic were plated on culture plates pre-coated with poly-d-lysine at a concentration of $1 \times 10^4$ cells per $cm^2$. Cultures were kept at 37° C. and 5% $CO_2$.

Glutamate Excitotoxicity

Figure 4:
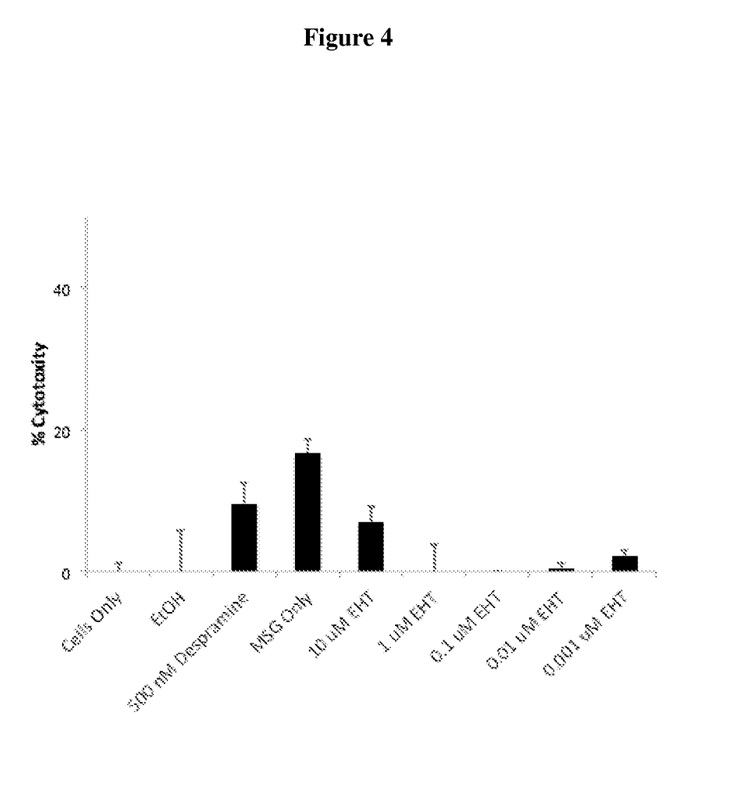
FIG. 4 demonstrates the reduced neuronal cytotoxicity induced by glutamate observed upon treatment with EHT extract in a dose dependent fashion.

Primary cortical neurons, were co-treated with 10 uM glutamate in the presence or absence of an EHT extract prepared according to Example 1; despramine was used as a positive control. After 24 hours at 37° C. and 5% $CO_2$, cellular viability was determined by measuring activity of lactate dehydrogenase in the culture supernatant according to the manufacturer's protocol (Roche). FIG. 4 demonstrates the reduced neuronal cytotoxicity induced by glutamate observed upon treatment with EHT extract in a dose dependent fashion.

It was unknown as to whether EHT extract or eicosanoyl-5-hydroxytryptamide exhibits neuroprotective properties towards excitotoxic cell death. EHT extract exhibits superior potency towards the neuroprotection of rat cortical neurons when compared to previously reported memantine dose-response curves in a similar experimental format for glutamate excitotoxicity.

What is claimed is:

1. A composition comprising an EHT extract comprising a mixture of late eluting tryptamides and early eluting tryptamides in a weight ratio of at least about 7:1 late eluting tryptamides:early eluting tryptamides, wherein the composition includes at least 30% eicosanoyl-5-hydroxytryptamide, based on the total weight of the tryptamides in the composition, wherein the amount of diterpenes in the composition is less than about 1 mg/kg of the composition and wherein the amount of caffeine does not exceed about 5%, based on the total weight of the extract.

2. The composition of claim 1, having a weight ratio of at least about 8:1 late eluting tryptamides:early eluting tryptamides.

3. The composition of claim 1, having a weight ratio of at least about 25:1 late eluting tryptamides:early eluting tryptamides.

4. The composition of claim 1, having a weight ratio of at least about 50:1 late eluting tryptamides:early eluting tryptamides.

5. The composition of claim 1, having a weight ratio of at least about 100:1 late eluting tryptamides:early eluting tryptamides.

6. The composition of claim 1, including at least 35% eicosanoyl-5-hydroxytryptamide, based on the total weight of the tryptamides in the composition.

7. The composition of claim 1, including at least 40% eicosanoyl-5-hydroxytryptamide, based on the total weight of the tryptamides in the composition.

8. The composition of claim 1, including at least 50% eicosanoyl-5-hydroxytryptamide, based on the total weight of the tryptamides in the composition.

9. The composition of claim 1, wherein the composition contains less than 10 mg of caffeine per serving or unit dosage of the composition.

10. The composition of claim 1, wherein the composition contains less than about 0.12 mg of cafestol per serving or unit dosage of the composition.

11. The composition of claim 10, wherein the composition contains less than about 0.06 mg of kaweol per serving or unit dosage of the composition.

12. The composition of claim 11, wherein the composition is a solid dosage form.

13. The composition of claim 12, wherein the solid dosage form is selected from the group consisting of: a tablet, a capsule, a sachet, a powder, and in the form of a solid food.

14. The composition of claim 13, further comprising one or more of a vitamin, a microelement, a food or health supplement, an herb extract, and a drug selected from the group consisting of piracetam, ADHD medications, xanthines, nicotine, tianeptine, cholinergic agents, valproates, pramiracetam, oxiracetam, coluracetam, and aniracetam.

* * * * *